US011326140B2

(12) United States Patent
Yerden (10) Patent No.: US 11,326,140 B2
(45) Date of Patent: May 10, 2022

(54) ASEPTIC CELL PROCESSING AND PRODUCTION WITH NO CHEMICAL BIOCIDES

(71) Applicant: Biospherix Ltd., Parish, NY (US)

(72) Inventor: Randy Yerden, Parish, NY (US)

(73) Assignee: Biospherix Ltd., Parish, NY (US)

( * ) Notice: Subject to any disclaimer, the term of this patent is extended or adjusted under 35 U.S.C. 154(b) by 0 days.

(21) Appl. No.: 17/179,468

(22) Filed: Feb. 19, 2021

(65) Prior Publication Data

US 2021/0171894 A1 Jun. 10, 2021

Related U.S. Application Data

(63) Continuation of application No. PCT/US2020/056836, filed on Oct. 22, 2020.

(60) Provisional application No. 62/924,322, filed on Oct. 22, 2019.

(51) Int. Cl.
| | |
|---|---|
| *C12M 1/12* | (2006.01) |
| *C12M 1/34* | (2006.01) |
| *C12M 1/00* | (2006.01) |
| *C12Q 1/22* | (2006.01) |
| *C12N 5/00* | (2006.01) |
| *C12N 5/071* | (2010.01) |

(52) U.S. Cl.
CPC ............ *C12M 37/04* (2013.01); *C12M 41/12* (2013.01); *C12M 45/03* (2013.01); *C12N 5/0081* (2013.01); *C12N 5/0602* (2013.01); *C12Q 1/22* (2013.01); *C12N 2500/02* (2013.01); *C12N 2523/00* (2013.01)

(58) Field of Classification Search
CPC ...... C12M 37/00; C12M 37/04; C12M 41/12; C12M 41/34; C12M 45/03; C12Q 1/22; C12N 2500/02; C12N 2523/00; C12N 5/0081; C12N 5/0602
See application file for complete search history.

(56) References Cited

U.S. PATENT DOCUMENTS

| | | | |
|---|---|---|---|
| 5,482,684 A * | 1/1996 | Martens | A61L 2/14 422/119 |
| 7,867,762 B2 | 1/2011 | Stahl et al. | |
| 2003/0092178 A1 | 5/2003 | Yerden | |
| 2011/0286883 A1 | 11/2011 | Hecht et al. | |
| 2015/0376833 A1* | 12/2015 | Paripati | C07G 1/00 435/99 |
| 2018/0079999 A1 | 3/2018 | Blanchard | |
| 2020/0010792 A1 | 1/2020 | Golway et al. | |
| 2020/0199518 A1 | 6/2020 | Kawasaki et al. | |

FOREIGN PATENT DOCUMENTS

| | | |
|---|---|---|
| WO | 2010/047672 A1 | 4/2010 |
| WO | 2012/058456 A2 | 5/2012 |

OTHER PUBLICATIONS

H.C. Pappas et al, "Self-Sterilizing, Self Cleaning Mixed Polymeric Multifunctional Antimicrobrial Surfaces," ACS Appl. Mater. Interfaces, 2015 750, 27632-27638, https://doi.org/10.1021/acsami.5b06852.
David J. Weber and William A. Rutala, "Self-disinfecting surfaces: Review of current methodologies and future prospects," Am. J. Infection Control 2013, 41(5, May 1) Supplement S31-S35, https://doi.org/10.1016/j.ajic.2012.12.005.
Xu Q, Zhang W, Dong C, Sreeprasad TS, Xia Z. "Biomimetic self-cleaning surfaces: synthesis, mechanism and applications," J. R. Soc. Interface 2016 13: 20160300. https://dx.doi.org/10.1098/rsif.2016.0300.
Brühwasser C, Heinrich H, Lass-Flörl C, Mayr A. Self-disinfecting surfaces and activity against *Staphyloccocus aureus* ATCC 6538 under real-life conditions. J Hosp Infect. Oct. 2017;97(2):196-199. doi: 10.1016/j.hin.2017.06.022. Epub Jun. 22, 2017. PMID: 28647424.
"Self-disinfecting surfaces: promising but not there yet" GAMA Healthcare News, Jul. 18, 2017.
M.M. Querido, et al., "Self-disinfecting surfaces and infection control," Colloids and Surfaces B: Biointerfaces, 2019, 178, 8-21, http://doi.org/10.1016/j.colsurfb.2019.02.009.
William A. Rutala, and David J. Weber, "Best practices for disinfection of noncritical environmental surfaces and eqiupment in health care facilities: A bundle approach," Sate of Science Rev., 2019, 47, Suppl, A96-A105, published Jun. 1, 2019, DOI:https://doi.org/10.1016/j.ajic.2019.01.014.
Terry Ann Else, Curtis R. Pantle, Penny S. Amy, "Boundaries for Biofilm Formation: Humidity and Temperature," Appl. Environ. Microbiol, 2003, 69 (8) 5006-5010; DOI:10.1128/AEM.69.8.5006-5010.2003.
John D. Coppin, et al., "Self-sanitizing coppper-impregnated surfaces for bioburden reduction in patient rooms," Am. J. Infection Control, 2017, 45(6) 692-694 publ. Jun. 1, 2017, https://doi.org/10.1016/j.ajic.2017.01.012.

\* cited by examiner

*Primary Examiner* — Blaine Lankford
(74) *Attorney, Agent, or Firm* — Gallet Dreyer & Berkey LLP; Andrew Berks (57) ABSTRACT

A method and apparatus of aseptic processing and production of cells in a non-sterile enclosure apparatus without chemical biocides is disclosed, by controlling the level of humidity throughout the enclosure to 25% relative humidity (RH) or less, and preferably 20% or 15% or less RH. In addition, the temperature is controlled to 37° C., and consistent gas flow is maintained the enclosure. Colony forming units from microbial contamination detected by environmental monitoring within the enclosure are significantly reduced in this method.

17 Claims, 5 Drawing Sheets

ASEPTIC CELL PROCESSING AND PRODUCTION WITH NO CHEMICAL BIOCIDES

CROSS REFERENCE TO RELATED APPLICATION

This application claims the benefit under 35 U.S.C. § 120 of PCT International patent application PCT/US20/56836, filed Oct. 22, 2020, and claims priority to U.S. Patent Application 62/924,322, filed Oct. 22, 2019, the entire contents of which is incorporated by reference.

FIELD OF THE INVENTION

This disclosure pertains to a method of processing and production of cells aseptically in non-sterile apparatus by adjustments of humidity, temperature, and air flow without the use of chemical biocides, and without exposing the cells to suboptimal conditions.

BACKGROUND

Cell culture is the process by which cells, typically but not exclusively mammalian cells are grown and handled under controlled conditions outside their natural environment in the body. After the cells of interest have been isolated from living tissue, they can subsequently be maintained under carefully controlled conditions. These conditions vary for each cell type, but generally consist of a suitable vessel with a substrate or medium that supplies the essential nutrients (amino acids, carbohydrates, vitamins, minerals), growth factors, hormones, and gases ($CO_2$, $O_2$), and regulation of the physio-chemical environment (pH buffer, osmotic pressure, temperature) at optimum levels for those cells.

Cells are used in drug discovery, cancer biology, regenerative medicine development, and basic life science research, to name a few of many applications in research. Industrially cells are also used for vaccine and biologics production, cell therapies, and cell-based gene therapies.

Growing cells ex vivo is technically challenging. To maintain the health and quality of living cells, the needs of cells must be fully supported to the extent possible. For example, cells grown ex vivo have no immune system to protect them from microbes, so protection against microbial contamination is required. Cells outside the body no longer have the body to keep conditions optimal. Temperature, pH, osmolarity, oxygen, carbon dioxide, etc. must be controlled at optimal levels outside the body or cells will degenerate and die. Conventional equipment only provides part time optimization, only inside incubators or bioreactors. For example, oxygen concentration is a critical parameter for cell processing and production. Cells inside the body never see oxygen levels as high as air oxygen. Physiologic oxygen levels are much lower, and they do not fluctuate in the body. Air oxygen levels are not physiologic and can damage cells. Accordingly, growing and processing cells ex vivo requires special environmental conditions that must be strictly controlled.

In some implementations, cells are grown in specialized isolation chambers specifically adapted to cell processing, manipulation, and production applications. For example, such isolation chambers may include a set of modular interconnected chambers, co-chambers, and sub-chambers configured to enclose all steps of a cell production process or series of cell process steps and compartmentalize in order to isolate certain individual steps from adjacent steps. An example of such equipment is the XVIVO SYSTEM® produced by BioSpherix Ltd, of Parish, New York. The XVIVO SYSTEM® provides a set of modular chambers, boxes, glove boxes, cabinets, sensors, environmental regulation apparatus, and other equipment specifically for cell culture, processing, and production applications. Since cells cannot be terminally sterilized, they must be produced by aseptic processing.

Separating cells ex vivo from room air and the people handling them using a physical barrier such as an isolator, or glove box, or other similar type of enclosures, dramatically reduces the chance of microbial contaminants reaching cells in culture. However, microbes can be entrapped inside upon the initial closing of the enclosure, and can enter a controlled enclosure on the surfaces of materials and supplies brought into the enclosure on a routine basis. The use of chemical biocides (also termed "microbiocides") applied as liquid disinfectants in wipe-downs of internal surfaces of such enclosures, wipe-down of items moved into such enclosures, or applied as gaseous fumigations inside such enclosures is the typical microbial risk mitigation technique for creating a sterile or nearly sterile environment inside so cells can be aseptically processed and produced. The problem is that chemical biocides can be toxic and therefore dangerous to people, and may be toxic to all cells, including the desired cells in culture that require protection from microbial contamination.

SUMMARY OF THE INVENTION

This invention pertains to methods of maintaining a sterile or nearly sterile environment inside a controlled environment enclosure for aseptic cell processing and production without chemical biocides and without exposing cells to suboptimal conditions. This method without chemical biocides is as effective at enabling aseptic processing and production of cells as with chemical biocides, yet non-toxic for cells being processed and safe for personnel operating the cell processing equipment.

Microbes have susceptibilities to temperature (T) and relative humidity (RH). The inventor has found T and RH conditions that reduce and maintain the microbial bioburden inside enclosures to levels that enable aseptic processing and production of cells without the use of chemical disinfectants, without compromising the optimum conditions for the cells of interest.

In an embodiment, this invention provides a method and environment for aseptic processing and production of cells in non-sterile enclosure apparatus without biocides. The method may employ an enclosure apparatus providing a controlled environment optimal for ex vivo cultivation, growth, processing or transport of prokaryotic or eukaryotic cells, wherein atmospheric gases, relative humidity (RH), temperature, and gas circulation can be precisely controlled. In the method, the RH of the enclosure is maintained at 25% or less around the clock, except for intervals when higher RH required for steps in the cultivation, growth, processing or transport of cells is temporarily controlled to the lowest RH level necessary and shortest duration necessary only in the compartment necessary, and then immediately returning the RH to 25% or less. In embodiments, the RH may be maintained at 20% or less, 15% or less, 10% or less, or 5% or less. In an embodiment, the temperature of the enclosure may be warmed to about 37° C. to enhance microbial control yet not be suboptimal for cells. In an embodiment, a continuously flowing atmosphere not suboptimal for cells accelerates drying and mixes and homogenizes RH throughout the enclosure.

This method is useful, for example, after initial closure of the isolative apparatus, and after periodic opening and re-closures, wherein all areas and surfaces within the enclosure are rapidly dried to effectively mitigate microbial contamination risk for cell processing and production operations. The method is also useful when any material, items, or apparatus is moved into the enclosure from the external environment. Such entries are routine in the operation of enclosure chambers. In the method, the materials moved into the enclosure are rapidly dried.

The enclosure apparatus may be a set of interconnected chambers, co-chambers, and sub-chambers, compartmentalized by internal doors between chambers, permanently connected or temporarily connected, monolithic or modular. The enclosure apparatus may be stationary or mobile. The enclosure apparatus may be made of rigid or flexible walls, metal or plastic walls, or any combinations thereof. In an embodiment, the interior surfaces in the contained environment may be made from a material selected from polymers, metals, and glass. The interior surfaces may be hydrophobic or hydrophilic. The enclosure apparatus may be fitted with functional or physical inputs/outputs sealed through walls, either permanent or temporary. Functional inputs/outputs refers to, for example, wires or tubes between chambers in an enclosure apparatus or to the exterior of an enclosure apparatus. These can be electrical power conduits, communication wires, gas handling tubes, and the like.

In an embodiment, the atmospheric gases within the enclosure apparatus can be precisely controlled, and may be comprised of oxygen, nitrogen, carbon dioxide, nitric oxide, carbon monoxide; and wherein VOC's, particulates, and pressure can be precisely controlled. The atmosphere in the contained environment may have an oxygen level at 0.1% to 35% v/v, and carbon dioxide at 0.1% to 20% v/v depending of what is optimal for cells.

In an embodiment, cells are processed and produced inside the enclosure manually through sealed ports by gloves or telemanipulators or by integrated process and analytic machines or full or partial automation.

In an embodiment, the cells grown and processed in the enclosed environment are eukaryotic or prokaryotic cells. The eukaryotic cells may be mammalian or insect cells or other cells. The cells may be human or mouse cells or other cells. The cells may be fresh primary cultures, early passage cultures, or cell lines.

In an embodiment, after rapid drying, no measurable CFU's (colony forming units) are detected floating as measured by environmental monitoring comprising settle plates or active air sampling plates. Floating or suspended in the moving atmosphere is the dominant path for contamination of cells. The only CFU's detectable are strongly adhered to surfaces, as measured by contact plates, where they are sequestered away from the cells and statistically unlikely to contaminate cells.

DESCRIPTION OF THE DRAWINGS

FIG. 1 shows the log reduction from the Example of coupons (i.e., test surfaces) of polypropylene or stainless steel inoculated with *Pseudomonas aeruginosa*, and at various time intervals after exposure to the inventive conditions of 15% relative humidity (RH) and 37° C. in a controlled environment enclosure (an XVIVO SYSTEM chamber) or a conventional biological safety cabinet (BSC) at 40% RH and 21° C. Asterisks (*) denote significant within-group differences (compared to time 0) while pound (#) demonstrates significant between-group differences (different conditions) determined by two-way ANOVA followed by Bonferroni's multiple comparisons test (* or #, $p<0.05$;  or ##, $p<0.01$; * or ###, $p<0.001$; ****, $p<0.0001$).

FIG. 2 shows the log reduction of coupons inoculated with *Candida albicans*, a pathogenic yeast, under the same conditions as discussed for FIG. 1.

FIG. 3 shows the log reduction of coupons inoculated with *Staphylococcus aureus*, a Gram-positive, round-shaped bacterium that is a usual member of the microbiota of the body, but is implicated in a number of pathogenic illnesses, under the same conditions as discussed for FIG. 1.

FIG. 4 shows the log reduction of coupons inoculated with *Aspergillus brasiliensis*, a fungus ubiquitous in soil that is a common food contaminant, under the same conditions as discussed for FIG. 1.

FIG. 5 shows the log reduction of coupons inoculated with *Bacillus subtilis*, a Gram-positive, catalase-positive bacterium, found in soil and the gastrointestinal tract of ruminants and humans, under the same conditions as discussed for FIG. 1. This bacteria can form a tough, protective endospore, allowing it to tolerate extreme environmental conditions.

FIG. 6 summarizes the log reductions in CFU's for the organisms studied in the Example on polypropylene and stainless steel test surfaces.

FIG. 7 shows the log reduction of *S. aureas* inoculated on polypropylene or stainless steel coupons at various relative humidity (RH) levels and 37° C. in a controlled environment enclosure. Asterisks (*) denote significant between-group differences between 37° C./5% RH group and 21° C./40% RH group determined by two-way ANOVA followed by Sidak multiple comparisons test (*, $p<0.05$).

FIG. 8 shows the log reduction of *S. aureas* inoculated on polypropylene or stainless steel coupons at various temperature levels and 15% RH in a controlled environment enclosure. Asterisks (*) denote significant within-group differences determined by two-way ANOVA followed by Sidak's multiple comparisons test (*, $p<0.05$; , $p<0.01$; *, $p<0.001$; ****, $p<0.0001$).

FIG. 9 is a photo of the experiment detailed in Example 2, showing a PBI Air Sampler adjacent to a centrifuge tube with a contaminated cap to test for airborne *B. subtilis* from the dried cap.

FIG. 10 is an alternative view of the same experiment as shown in FIG. 9. This view shows the faceplate/air intake on the Air Sampler device.

DETAILED DESCRIPTION

This invention provides an environment for aseptically processing and producing cells optimized for cellular existence outside the body (except frozen), particularly in multi-compartment isolative chambers and enclosures. The term "cellular existence" refers to all of the only four states of existence of cells outside the body:

1. Cells proliferating or not proliferating in a state of incubation;
2. Cells being handled or manipulated;
3. Cells being processed or analyzed in some kind of machine;
4. Transport of cells between any of the above three states.

The environments used for such cellular manipulations may be in an enclosure apparatus that may comprise a set of interconnected chambers, co-chambers, and sub-chambers, compartmentalized by internal doors between chambers, permanently connected or temporarily connected, monolithic or modular. The enclosure apparatus may be fixed or mobile.

In the inventive method, rapid extreme drying is the primary physical mechanism used to create and maintain an aseptic or nearly aseptic environment desirable for cells. Extreme drying can kill most microbes and prevent the growth of all others. A small proportion of microbes can be resistant to desiccation. If none of these end up inside the enclosure, this method maintains aseptic conditions. If some desiccation resistant microbes end up inside, this method maintains nearly aseptic conditions, yet still enables aseptic cell processing due to immobilization of the viable microbes on surfaces, thereby sequestering them away from cells. It is accomplished by controlling the level of humidity throughout the entire system, to an extremely low level, less than 25% relative humidity (RH), and preferably 20% or 15% or less RH. In addition, continuous pervasive temperature control throughout at 37° C. enhances the microbicidal effectiveness of desiccating humidity levels at these low RH levels. In addition, a moving internal atmosphere accelerates drying and homogenizes antimicrobial conditions throughout enclosure. Optionally, variable controlled oxygen and variable controlled carbon dioxide necessary for optimizing conditions for cells does not interfere with this disinfection protocol. As used herein, the term "microbe" refers to any undesired contaminating organism, for example undesirable bacteria or fungi that can contaminate cell cultures.

Whenever high humidity levels are required for a step in a process pertaining to cellular existence, the RH is strictly controlled at minimally necessary levels only in the compartment necessary for only the minimum time necessary, and then immediately returned to desiccating levels. Whenever lower temperatures are required, they are strictly controlled at no lower than necessary only in the compartment necessary for only the time necessary, and then immediately returned to 37° C. Temperatures higher than 37° C. enhance microbial kill, but are not necessary. Data shows this method tips the balance successfully to a radical reduction in contamination risk simultaneously with a radical reduction in use of risky chemical biocides while not exposing cells to suboptimal conditions.

In an embodiment, the RH, temperature, and flowing atmosphere may be controlled for each chamber independently of any other chamber in the enclosure apparatus. For example, a cell optimization protocol requiring a lower temperature or higher humidity could be performed in one particular chamber in a multi-chamber apparatus, while other chambers maintain the inventive conditions of low RH and elevated temperature. In an embodiment, the environment of each chamber in a multichamber enclosure apparatus can be controlled independently of any other chamber.

Significantly, no chemical biocides (liquids or gases) are used in the inventive method. Examples of liquid chemical biocides include isopropyl alcohol, quaternary ammonium salts, bleach, etc. Examples of gaseous chemical biocides include vaporized hydrogen peroxide, chlorine dioxide, formaldehyde, etc. None are necessary. The inventor has discovered that low humidity, elevated temperature, and turbulent or laminar gas flow can sufficiently sanitize internal environment including the atmosphere and surfaces in enclosures and chambers optimized for cells.

Presumably, the low humidity conditions of this invention kills most microbial organisms because they are sensitive to desiccation, and for organisms capable of surviving low humidity and elevated temperatures, for example from spore forming bacteria and fungi, all microbes including such organisms were discovered to be immobilized on internal surfaces by strong adhesion to such surfaces. Furthermore, the gas flow used in the inventive method accelerates microbial drying and ensures that the desiccating and warm conditions penetrate to all corners and recesses within the interior of an enclosure apparatus. Spores or other potentially infectious particles immobilized on surfaces by rapid drying under desiccating conditions are not a measurable contamination risk for cells processed and produced in the enclosures used in this invention.

The inventive method does not require chemical sterilization of the chamber or enclosure in advance, does not require a disinfectant wipe-down of inside surfaces in any part of the system, does not require a disinfectant wipe down of any materials or equipment moved into the enclosure, and does not require internal washing to reliably process and produce cells aseptically. The inventive method disinfects and cleans the interior of an enclosure apparatus sufficiently so that no colony forming units (CFUs) can be detected floating inside as evidenced by intensive environmental monitoring with settle plates and active air sampling plates. With this invention, over time, an enclosure becomes progressively more aseptic. However, the inventive method is not incompatible with the use of chemical biocides and may be synergistic with cautious biocide treatment that does not endanger the cells.

Contact plates (also termed "touch plates") are used for monitoring microbial contamination of surfaces. These plates have an agar medium poured into petri dish, and the agar can be contacted with a surface in a chamber. Any microbial contamination on the test surface will adhere to the agar. The agar is then incubated and the microbial contamination will grow, which are termed "colony forming units" (CFU's), which can be counted to quantify the degree of contamination on the test surface. Settle plates are similar and are used for passive air monitoring. An agar plate in a petri is exposed to an environment for a measured length of time. Airborne microbial particles will land on the agar. The plate is then incubated and CFU's can be counted. Active air sampling plates employ an air sampler to physically draw a pre-determined volume of air and pass it over the agar. The plate is then removed from the air sampler and directly incubated. These were used to develop the method.

In this invention, no CFUs are detected by any of these three methods if no desiccation resistant microbes happen to be inside, wherein the inventive method actually sterilizes the enclosure and makes the enclosure aseptic. However, if any desiccation resistant microbes happen to be inside, no CFUs will be detected in only settle plates and active sample plates because immobilization assures whatever few desiccation resistant microbes might be in a chamber subject to the inventive physical conditions, they are prevented from floating by adhesion to a surface. Such desiccation resistant microbes may be viable and could be detected by contact plates. In this case the inventive method doesn't create an aseptic environment, or aseptic conditions inside the enclosure, or a sterile enclosure, because it is not sterile inside, only nearly sterile, or nearly aseptic. Inventively, however, it does enable aseptic processing because the only microbes viable and capable of contaminating the cells are sequestered to a surface. They can transfer to other surfaces by touch but they don't detach from these other surfaces. Therefore, there is no path to contaminate cells because the practice of sterile technique assures that these few microbes will have no sequential touch points to any surfaces that will touch the cells or substrates of the cells.

The inventive method may be used, for example, after the initial installation and closure of an enclosure apparatus, and after periodic opening and re-closures. Such an apparatus may comprise a set of interconnected chambers, co-chambers, and sub-chambers, compartmentalized by internal doors between chambers, permanently connected or temporarily connected, monolithic or modular. The enclosure apparatus may be fixed or mobile. The enclosure apparatus may be made of rigid or flexible walls, metal or plastic walls, or any combinations thereof.

The inventive method may also be also use for frequent operations where materials, items, and equipment are routinely moved into an enclosure apparatus. Such routine operations are typically the single source of new microbial contamination risk. But with the rapidly desiccating conditions as provided herein, microbes on these materials and equipment are immobilized within minutes, and most are killed within hours.

The traditional reliance on frequent application and over-use of strong liquid and gaseous chemical biocides to achieve aseptic processing and production is highly risky for the desired cells. Furthermore, biocide use is inherently intermittent. The biocide (liquid or gas) is applied and then stopped. In between, there is no antimicrobial activity, providing a window for undesirable microbes to grow and contaminate equipment and cell cultures within the enclosure. By contrast, this physical approach is constant, with continuous antimicrobial activity maintained 24/7.

Furthermore, unlike liquid biocide effectiveness limited by surface coverage, this physical approach acts like a gas. It reaches into every nook and cranny inside the entire system, especially when driven by gas flow patterns inside the chambers. All interior surfaces in a chamber, whether reachable or unreachable, including inside every crack, seam, crevice, and cavity are permeated with this antimicrobial action continually. Finally, instead of concern with surface residuals and off-gases and toxic vapors left after each chemical biocide application, this alternative approach leaves no residuals or any toxic off-gases or vapors because it's a physical approach—desiccation at temperatures elevated above room air conditions accelerated by a moving atmosphere.

In an embodiment, gas flow within an enclosure apparatus may be an important feature in this invention. Gas flow can be turbulent or laminar. Gas flow relies on a fan that recirculates the controlled atmosphere within each isolated chamber to create some degree of turbulence within the chamber. In an embodiment, the gases being recirculated may also pass through a HEPA filter. Alternatively, gas flow may be laminar, meaning a steady flow in a single direction.

The RH levels, temperature, and gas flow in this invention may be controlled as other environmental parameters in an isolated chamber apparatus are controlled. For example, RH can be controlled using dry gases from gas tanks, which are supplied in a highly purified state with no moisture. RH can also be controlled in established atmospheres using a recirculation fan that passes the gases in an enclosure over regenerable chemical desiccants (for example, silica gel or calcium sulfate) and back into the enclosure. RH can also be controlled by electronic or compressor dehumidifiers. In addition, a HEPA filter may be used in such a recirculation system.

In an embodiment, the drying effect as described herein may be rapid, meaning that when an object is moved into a chamber from an external environment, the humidity and any surface moisture on the object is dried to the point that contaminating microbes are immobilized within minutes and killed within hours, to achieve the killing or adhesion of microbial contaminants as disclosed herein. This rapid drying minimizes the ability of contaminants to become airborne within the chamber eliminating the major path whereby microbes can contaminate cells.

Microbes can be entrapped inside an enclosure apparatus during assembly and installation, and can be entrapped after periodic opening and re-closure of part of a system or entire system. With this method the contamination risk they present drops continuously over time since none can reproduce, and most are killed by desiccation. However, a small percentage of microbes entrapped may be desiccation resistant. Their incidence is likely to be different at different sites, and likely to vary at each location over the seasons. Any that become detached and float immediately get removed from the processing area and sequestered permanently in a remote filter, thereby eliminating them as a risk to the cells. The few that might remain attached to an internal surface are not a measurable risk for the same reason, because they get sequestered to that surface. Under normal operating conditions, the incidence of these residual sequestered viable microbes is so small that within a few days no CFUs can be detected inside by intensive environmental monitoring, not only with settle plates and active air sampling plates, but contact plates as well.

Thereafter the only new bioburden risk comes from surfaces of materials brought into the system. Bioburden here is defined as the number of bacteria living on a surface of the incoming items. Risk is highest near the entry point but drops precipitously to undetectable levels along the first few sequential points of contact with those materials as they are moved in. Rapid drying sufficiently mitigates all detectable floating CFU risk, including desiccation resistant microbes. No gas or liquid chemical biocides are required to routinely produce cells aseptically.

In an embodiment, the atmosphere in the contained environment having an oxygen level at 0.1% to 35% v/v, and carbon dioxide at 0.1% to 20% v/v, with the balance nitrogen. Other gases possibly employed in cellular processing and production protocols in the contained environments described in this invention may include nitric oxide and carbon monoxide. Other atmospheric features that can be controlled are volatile organic compounds (VOC's) which may be introduced from biocide materials, particulates in the atmosphere of a chamber, and atmospheric pressure.

In an embodiment, the interior surfaces in the chamber with the controlled environment are hydrophobic or hydrophilic. In an embodiment, the interior surfaces in the contained environment may be made from polypropylene or stainless steel. Additional materials are within the scope of this invention, including polyethylene or other rigid plastics, glass, aluminum, and other polished or painted metallic materials.

In an embodiment, the cells processed and produced within the controlled environment are eukaryotic cells, which includes mammalian cells, for example, freshly biopsied primary cultures, or early passage cultures from various tissue, or cell lines such as GH3 (rat pituitary tumor) and PC12 (rat pheochromocytoma). In an embodiment, the eukaryotic cells in the chamber with the controlled environment are human cells, for example, freshly biopsied primary cultures, early passage cultures, or cell lines MCF-7 (breast cancer), MDA-MB-468 (breast cancer), PC3 (prostate cancer), and SaOS-2 (bone cancer) (representative examples only). In an embodiment, the cells may be plant cells, or insect cells, or prokaryote cells.

Example 1

Organisms and Media. The following organisms were tested in the inventive method: *Pseudomonas aeruginosa, Staphylococcus aureus, Bacillus subtilis, Aspergillus brasiliensis* and *Candida albicans* from BIOBALL® (BIOMERIEUX (Hazelwood, Mo.). CFU were assayed on culture plates containing Tryptic Soy Agar from Sigma (St. Louis, Mo.). *A. brasiliensis* plates were cultured at 25° C. for 36-48 hrs while the other organisms were cultured at 35° C. for 20-24 hrs before colony assessment. For environmental monitoring, contact plates were made of BBL™ Trypticase™ Soy Agar from BD (Sparks, Md.). Contact plates were incubated at 35° C. for at least 20-24 hrs.

Coupon Inoculation. Coupons (10 mm diameter) were made of polypropylene, or stainless steel (Beadthoven Jewelry on Amazon.com). The coupons were triple-cleaned/ disinfected, in TexQ (Texwipe, www.texwipe.com), then SporKlenz (Steris, Inc. www.steris.com), then 70% ethanol for 30-60 min each soak, with a triple $ddH_2O$ rinse between each disinfectant. They were air dried in a laminar flow hood. Dried coupons were stored in sterile 50 ml conical tubes (CELLTREAT Scientific Products; Pepperell, Mass.) at RT.

Microbial Reduction Assays. At least one day prior to these studies, the probable risk surfaces in the chamber were disinfected with SporKlenz (Steris, Inc. www.steris.com) and atmospheric gases were replaced with fresh triple-filtered dry tanked gases (20%$O_2$, 0.1% $CO_2$, balance $N_2$) to eliminate any disinfectant fumes. Triple-cleaned/disinfected coupons were inoculated in place on the PC floor as if a drop of bacterial culture had contaminated the work surface. Inoculated coupons were exposed to experimental conditions and collected at time intervals. Harvested coupons were placed in 1 ml 0.05% Tween-80 in DPBS and vortexed 5×10 seconds. Microbial suspensions were diluted further before being spread on agar plates. Colonies on each plate were counted by two individuals who were blinded to experimental conditions. At 10% or greater discrepancy, a third person re-counted colonies. The mean of two closer numbers was used for data analysis. Log reduction was calculated using equation: $R_i$=log $(Y_0)$–log $(Y_i)$. $R_i$ is log reduction for each time point, where $Y_0$ is remaining microbes at time zero, and $Y_i$ is remaining microbes at time i. All statistical analyses were performed using GraphPad Prism (Version 8.4.2, GraphPad Software, Inc.) as described in figure legends. Data are expressed as the mean+SEM. Significance was assessed at $p<0.05$.

The inventive conditions produce larger microbial reductions than room air BSC conditions in a microbe-dependent manner. The experimental hypothesis was that there would be differences between microbial infectivity in controlled enclosure conditions and conventional room air biological safety cabinet (BSC) conditions. The coupons described above (polypropylene or stainless steel) were inoculated with known number of microbes in each chamber and incubated either in an XVIVO System processing chamber under inventive conditions (37° C./15% RH), or a processing chamber set to conventional room air BSC conditions (21° C./40% RH). Coupons were collected at intervals and assayed for remaining viable colony-forming units (CFU). Data from 3 or more independent experiments were combined for comparisons. Statistically significant log reductions in CFU were found on four out of five microbes in the two different conditions. These reductions were only from exposure to physical atmospheric conditions without the use of any antimicrobial chemicals.

Data showing differences in CFU recovered over time in each condition, as well as differences between conditions at various time points are shown in FIGS. 1-5 for both polypropylene and stainless steel test surfaces. *P. aeruginosa* (FIG. 1), *C. albicans* (FIG. 2), and *S. aureus* (FIG. 3) on both materials all demonstrated dramatic and significant log reductions in CFU's within the time frames studied under both inventive and room air BSC conditions. Results for *A. brasiliensis* (FIG. 4) were less dramatic but still significant. Consistent with its known resistance to environmental conditions, little CFU reduction was seen in *B. subtilis* spores (FIG. 5) in any condition tested. Comparing the microbial response to each condition separately (FIG. 6) the data clearly demonstrated a spectrum of microbial sensitivities to cell processing chamber conditions which were consistent with their known sensitivities to environmental conditions. These trends were similar between the two surface materials tested. Asterisks in FIG. 1-4 (*) denote significant within-group differences (compared to time 0) while pound (#) demonstrates significant between-group differences (different conditions) determined by two-way ANOVA followed by Bonferroni's multiple comparisons test (* or #, $p<0.05$;  or ##, $p<0.01$; * or ###, $p<0.001$; ****, $p<0.0001$).

Figure 7:
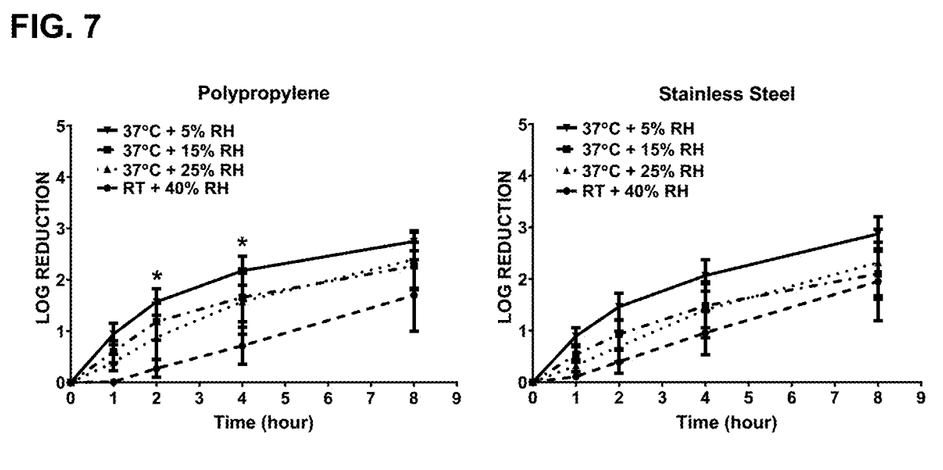
Figure 8:
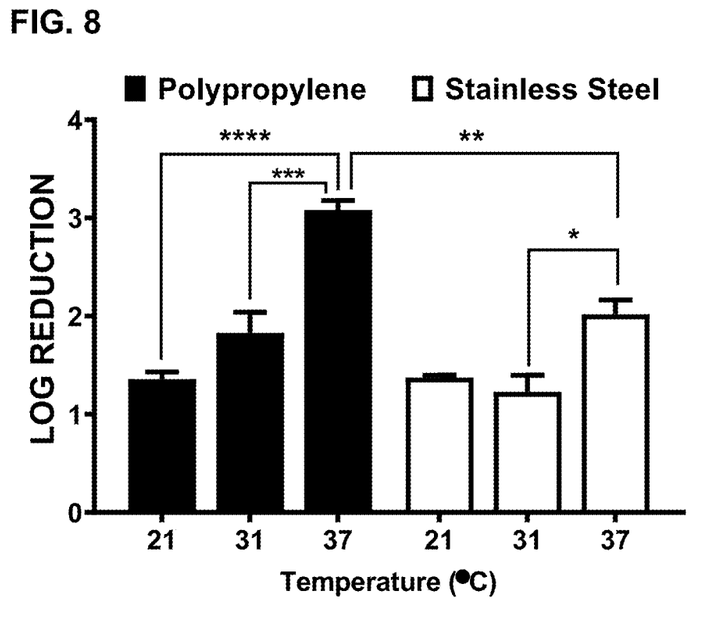

Various humidity levels in the controlled environmental chamber were also investigated (FIG. 7), from between 40% RH to 5% RH. Significant increases in log reductions of CFU's are clearly seen in both polypropylene and stainless steel as humidity decreases.

Figure 1:
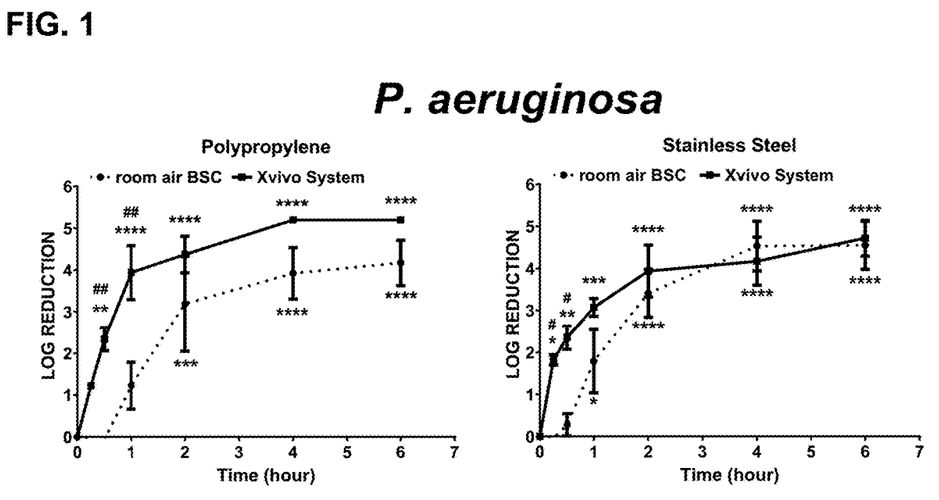
Figure 2:
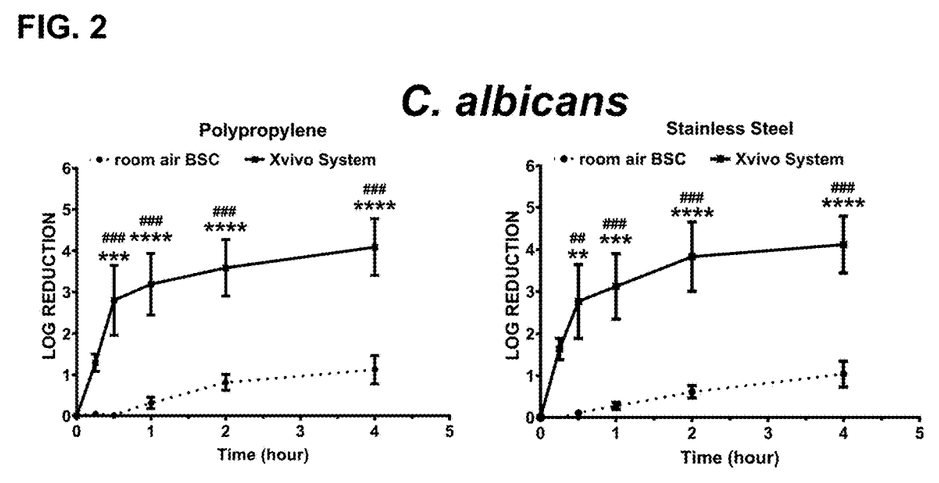
Figure 3:
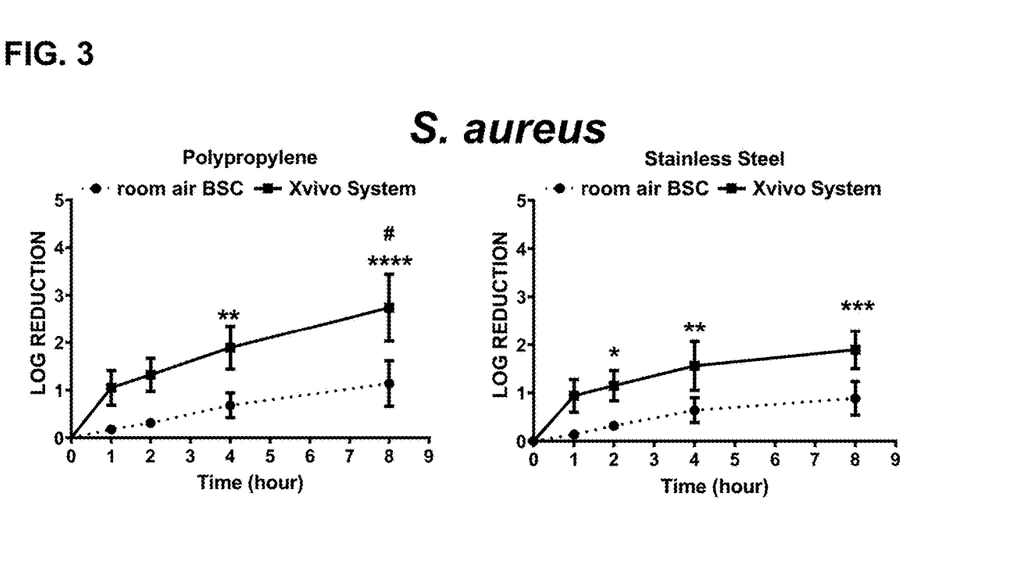
Figure 4:
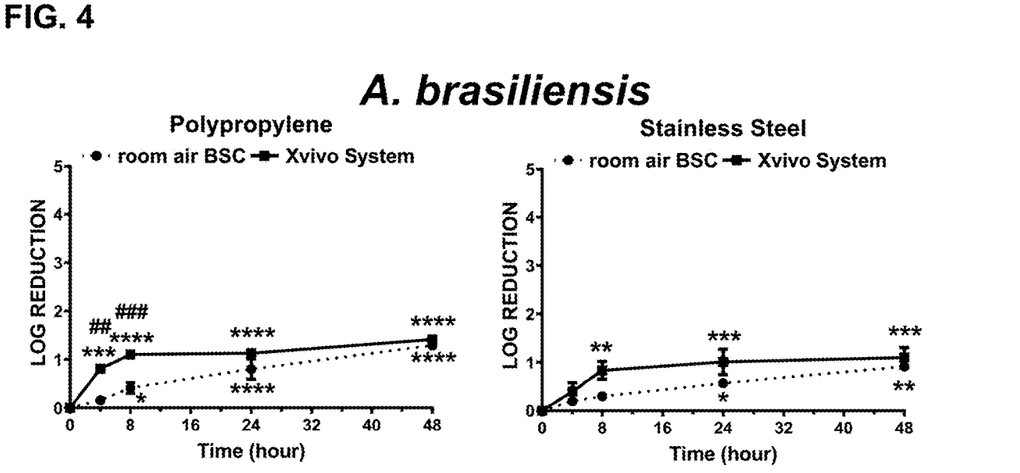
Figure 5:
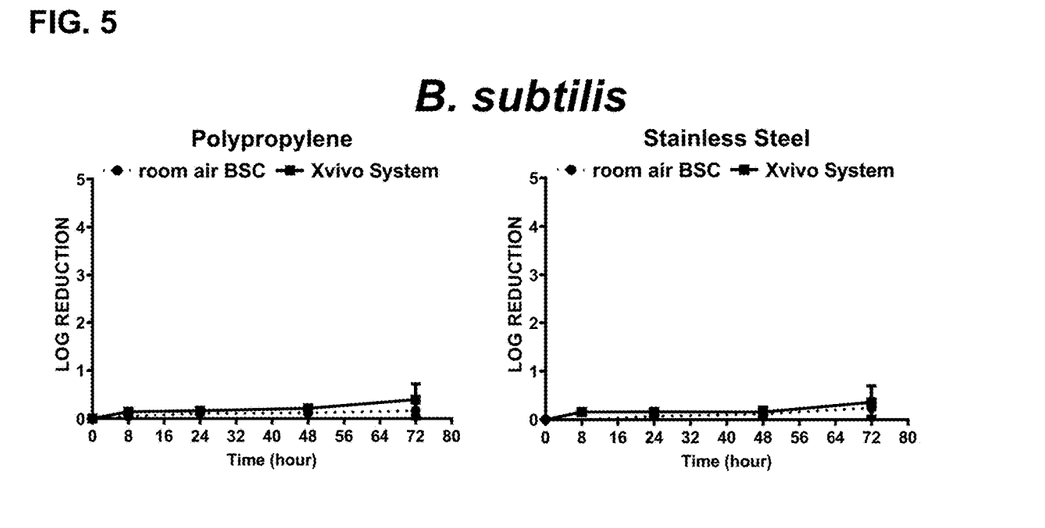
Figure 6:
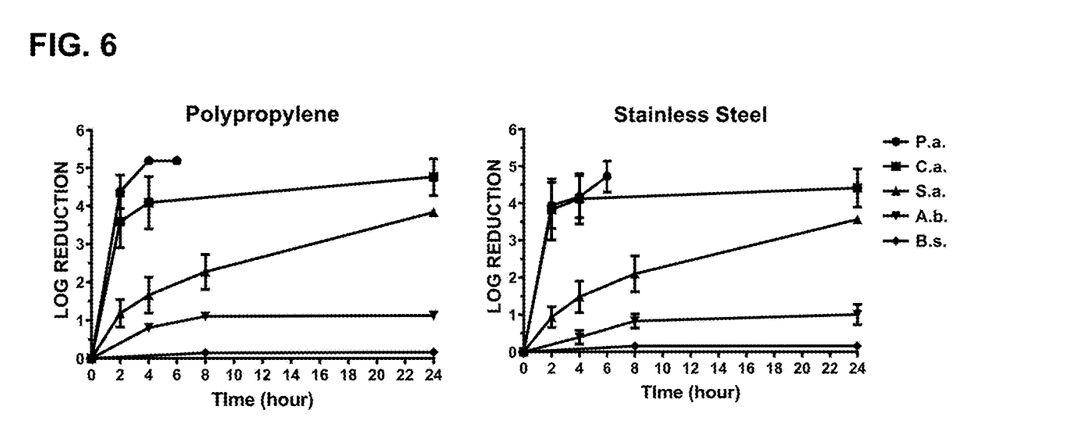

Various temperature levels were also investigated as shown in FIG. 6 for *S. aureas*. This data shows that increasing the temperature from 21° C. to 37° C. resulted in a significant reduction in CFU's detected.

Example 2

Airborne *B. subtilis* was quantified after rapid drying in the inventive method with active air sampling and passive air sampling (settle plates) in XVIVO SYSTEM enclosure.

Figure 9:
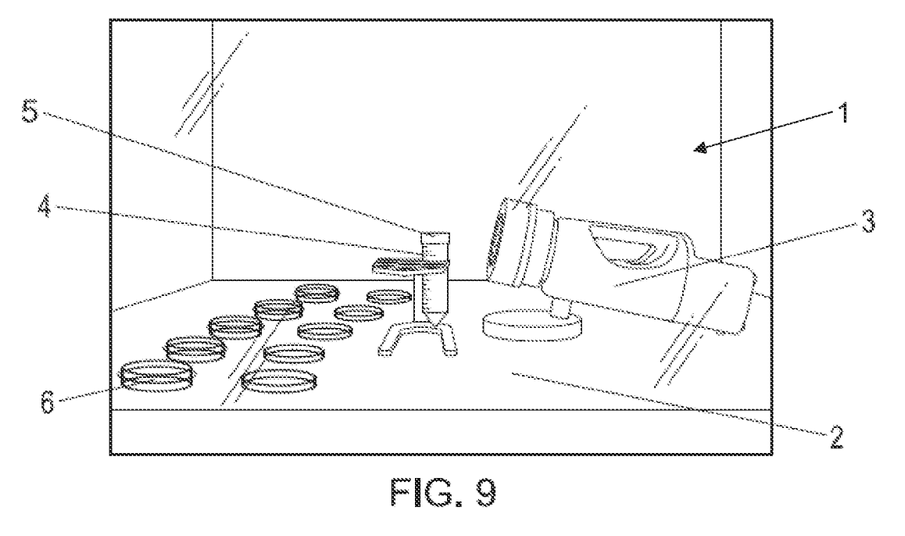
Figure 10:
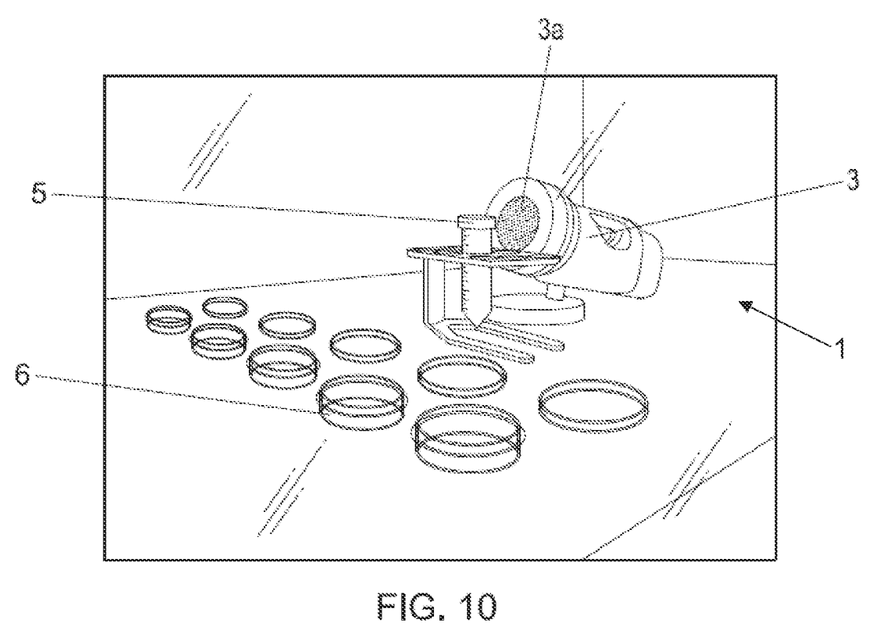

In an experiment set up as shown in FIGS. 9-10, an air sampling machine 3 ("PBI Air Sampler SAS Super 100") with faceplate/air intake 3a is set up in enclosure chamber 1 having enclosure floor 2. Centrifuge tube 4 having centrifuge tube cap 5 was placed within a few cm's of faceplate 3a just upstream of sample inlet. In addition, several passive air sampling settle plates of agar 6 were also positioned on the floor. The atmosphere handling arrangement in the enclosure chamber created gas flow turbulence in the chamber.

Cap 5 was contaminated with $10^7$ CFUs of *B. subtilis* in a tiny drop of saline and moved into the chamber with 15% RH at temperature 37° C., and with a turbulent atmosphere. Immediately after visible drying, which took about 11 minutes, the active air sampler with agar plates was used to quantify any *B. subtilis* that may have blown off the cap 5. Additional detection of *B. subtilis* used the array of agar settle plates 6 around the air sampler 3. No CFUs were detected over 4 hours in any plates. The active air sampling was set at 90 L/min and maintained for 4 hours with fresh plates every 20 minutes.

This experiment is typical of dozens of other experimental results confirming that rapidly dried microbes on surfaces are immobilized in-place and despite movement of the atmosphere they do not easily detach and they do not become airborne, although they will transfer from surface to surface upon contact of these surfaces.

The invention claimed is:

1. A method of aseptic processing and production of cells in a nearly aseptic enclosure apparatus without biocides comprising
   a. at least one chamber in an enclosure apparatus having a plurality of chambers providing a nearly aseptic environment adapted for optimal ex vivo cultivation, growth, processing or transport of prokaryotic or eukaryotic cells, wherein atmospheric gases, relative humidity (RH), temperature, and gas circulation can be precisely controlled;
   b. adjusting the RH of the at least one chamber to 20% or less with a nearly continuously flowing atmosphere optimal for cells to mix and homogenize the RH throughout the at least one chamber;
   c. adjusting the temperature of the at least one chamber to 37° C. or other elevated temperature optimal for cells;
   d. wherein the RH, temperature and flowing atmosphere within the at least one chamber elicits a physical antimicrobial effect to disinfect and clean the interior of an enclosure apparatus by rapid desiccation of any microbes floating or suspended in the atmosphere in the interior of the at least one chamber or on the interior walls or other surfaces of the at least one chamber, resulting in the death or immobilization by adhesion of all microbes on any surfaces in the at least one chamber, whereby microbial reproduction is prevented and no floating or airborne viable undesirable microbes can be detected;

e. wherein any higher RH in the at least one chamber required for the cultivation, growth, processing or transport of cells is controlled to the RH level no higher than necessary for the shortest duration necessary, and then immediately returning the RH to 20% or less;

f. wherein any lower temperature in the at least one chamber required for the cultivation, growth, processing, or transport of cells is controlled to the temperature no lower than necessary for the shortest duration necessary, and then immediately returning to the elevated temperature of about 37° C. optimal for cells; and g. wherein (i) upon initial closure and after each periodic opening and re-closure of the enclosure apparatus, all areas, atmosphere, and surfaces within the enclosure are rapidly dried; or (ii) any material or apparatus, when moved into the enclosure from the external environment is rapidly dried, to create and maintain an aseptic or nearly aseptic environment optimal for the ex vivo cultivation of cells.

2. The method of claim 1, wherein the relative humidity is controlled to 15% or less, or to 10% or less.

3. The method of claim 1, wherein the enclosure apparatus comprises two or more interconnected chambers, co-chambers, and sub-chambers, compartmentalized by internal doors between chambers, permanently connected or temporarily connected, monolithic or modular.

4. The method of claim 3, wherein the RH, temperature, and flowing atmosphere is controlled for each chamber independently of any other chamber in the enclosure apparatus.

5. The method of claim 1, wherein the enclosure apparatus is stationary or mobile.

6. The method of claim 1, wherein the enclosure apparatus is made of rigid or flexible walls, metal or plastic walls, or any combinations thereof.

7. The method of claim 1, wherein the interior surfaces are hydrophobic or hydrophilic.

8. The method of claim 1, further comprising interior surfaces in the contained environment made from a material selected from polyethylene, polypropylene, stainless steel, and glass.

9. The method of claim 1, wherein the enclosure apparatus is fitted with functional or physical inputs/outputs through walls, either permanent or temporary, either sealed or semi-sealed in passageways not compromising control inside enclosure.

10. The method of claim 1, wherein the atmospheric gases within the enclosure apparatus that can be precisely controlled comprise oxygen, nitrogen, carbon dioxide, nitric oxide, carbon monoxide; and wherein VOC's, particulates, and pressure can be precisely controlled.

11. The method of claim 1, further comprising an atmosphere in the contained environment having an oxygen level at 0.1% to 35% v/v, and carbon dioxide at 0.1% to 20% v/v.

12. The method of claim 1, wherein cells are processed and produced inside the enclosure manually by gloves or telemanipulators through sealed ports or by integrated process and analytic machines or by full or partial automation.

13. The method of claim 1, wherein the cells are eukaryotic cells.

14. The method of claim 13 wherein the eukaryotic cells are mammalian cells.

15. The method of claim 14, wherein the mammalian cells are human cells.

16. The method of claim 1, wherein no measurable CFU's (colony forming units) of desiccation resistant microbes are detected as measured by environmental monitoring with settle plates or active air sampling plates inside the enclosure.

17. The method of claim 1, wherein no measurable CFU's (colony forming units) of microbes susceptible to desiccation are detected as measured by environmental monitoring with settle plates, active air sampling plates, or contract plates.

* * * * *